US011097041B2

(12) United States Patent
Yeh et al.

(10) Patent No.: US 11,097,041 B2
(45) Date of Patent: Aug. 24, 2021

(54) NANOCLAY SORBENT METHODS FOR USE WITH DIALYSIS

(71) Applicants: BAXTER INTERNATIONAL INC., Deerfield, IL (US); BAXTER HEALTHCARE SA, Glattpark (CH)

(72) Inventors: Rosa H. Yeh, Libertyville, IL (US); Wei Xie, Indian Creek, IL (US); Hsinjin E. Yang, Long Grove, IL (US); Michael T. K. Ling, Vernon Hills, IL (US); Ying-Cheng Lo, Green Oaks, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 238 days.

(21) Appl. No.: 16/412,999

(22) Filed: May 15, 2019

(65) Prior Publication Data

US 2019/0262527 A1 Aug. 29, 2019

Related U.S. Application Data

(60) Division of application No. 15/816,550, filed on Nov. 17, 2017, now Pat. No. 10,342,912, which is a (Continued)

(51) Int. Cl.
*A61M 1/34* (2006.01)
*A61M 1/14* (2006.01)
(Continued)

(52) U.S. Cl.
CPC ............ *A61M 1/3486* (2014.02); *A61M 1/14* (2013.01); *A61M 1/16* (2013.01); *A61M 1/1696* (2013.01);
(Continued)

(58) Field of Classification Search
CPC ........ A61M 1/14; A61M 1/16; A61M 1/1621; A61M 1/1623; A61M 1/1625;
(Continued)

(56) References Cited

U.S. PATENT DOCUMENTS 3,388,803 A 6/1968 Scott
4,035,459 A 7/1977 Kesting
(Continued)

FOREIGN PATENT DOCUMENTS

EP 637616 2/1995
EP 1935441 A1 6/2008
(Continued)

OTHER PUBLICATIONS

R. Briell, Senior Scientist, "Nanoclays—Counting on Consistency," Southern Clay Products, Inc., 2006.
(Continued)

*Primary Examiner* — Shefali D Patel
(74) *Attorney, Agent, or Firm* — K&L Gates LLP

(57) ABSTRACT

Dialysis is enhanced by using nanoclay sorbents to better absorb body wastes in a flow-through system. The nanoclay sorbents, using montmorillonite, bentonite, and other clays, absorb significantly more ammonium, phosphate, and creatinine, and the like, than conventional sorbents. The montmorillonite, the bentonite, and the other clays may be used in wearable systems, in which a dialysis fluid is circulated through a filter with the nanoclay sorbents. Waste products are absorbed by the montmorillonite, the bentonite, and the other clays and the dialysis fluid is recycled to a patient's peritoneum. Using an ion-exchange capability of the montmorillonite, the bentonite, and the other clays, waste ions in the dialysis fluid are replaced with desirable ions, such as calcium, magnesium, and bicarbonate. The nanoclay sorbents are also useful for refreshing a dialysis fluid used in
(Continued)

hemodialysis and thus reducing a quantity of the dialysis fluid needed for the hemodialysis.

20 Claims, 4 Drawing Sheets

Related U.S. Application Data continuation of application No. 12/166,063, filed on Jul. 1, 2008, now Pat. No. 9,821,105.

(51) Int. Cl.
  *A61M 1/16*   (2006.01)
  *A61M 1/28*   (2006.01)
  *A61M 1/30*   (2006.01)

(52) U.S. Cl.
  CPC .............. *A61M 1/28* (2013.01); *A61M 1/34* (2013.01); *A61M 1/3406* (2014.02); *A61M 1/3472* (2013.01); *A61M 1/1619* (2014.02); *A61M 1/284* (2014.02); *A61M 1/30* (2013.01); *A61M 1/3413* (2013.01); *A61M 2202/0021* (2013.01); *A61M 2202/0028* (2013.01); *A61M 2202/0078* (2013.01); *A61M 2202/0498* (2013.01); *A61M 2205/0211* (2013.01); *A61M 2205/12* (2013.01); *A61M 2205/125* (2013.01); *A61M 2205/126* (2013.01); *A61M 2205/15* (2013.01); *A61M 2205/3331* (2013.01); *A61M 2205/3368* (2013.01); *A61M 2205/50* (2013.01); *A61M 2205/75* (2013.01); *A61M 2209/088* (2013.01); *A61M 2210/1017* (2013.01)

(58) Field of Classification Search
  CPC .............. A61M 1/1627; A61M 1/1654; A61M 1/1656; A61M 1/1672; A61M 1/1694; A61M 1/1696; A61M 1/28; A61M 1/284; A61M 1/287; A61M 1/34; A61M 1/3403; A61M 1/3406; A61M 1/3472; A61M 1/3475; A61M 1/3479; A61M 1/3486; A61M 2202/0021; A61M 2202/0028; A61M 2202/0042; A61M 2202/0078; A61M 2202/0498; A61M 2205/12; A61M 2205/125; A61M 2205/126; A61M 2205/75; A61M 2209/088; A61M 2210/1017; A61M 2205/0211
  See application file for complete search history.

(56) References Cited

U.S. PATENT DOCUMENTS

| | | | |
|---|---|---|---|
| 4,219,517 A | 8/1980 | Kesting | |
| 4,276,175 A | 6/1981 | Bower | |
| 5,284,470 A | 2/1994 | Beltz | |
| 5,403,485 A | 4/1995 | Dunweg et al. | |
| 5,498,338 A | 3/1996 | Kruger | |
| 5,656,372 A | 8/1997 | Gentile et al. | |
| 5,833,896 A | 11/1998 | Jacobs et al. | |
| 5,859,175 A | 1/1999 | Blatter et al. | |
| 5,869,033 A | 2/1999 | Schulz | |
| 5,938,929 A | 7/1999 | Shimagaki et al. | |
| 5,944,684 A | 8/1999 | Roberts et al. | |
| 6,103,117 A | 8/2000 | Shimagaki et al. | |
| 6,579,460 B1 | 6/2003 | Willis et al. | |
| 6,814,871 B1 | 11/2004 | Bem et al. | |
| 6,833,392 B1 | 12/2004 | Acquarulo, Jr. et al. | |
| 6,960,179 B2 | 11/2005 | Gura | |
| 7,034,071 B2 | 4/2006 | Acquarulo, Jr. et al. | |
| 7,083,854 B1* | 8/2006 | Joo | D01D 5/0007 428/364 |
| 7,182,870 B2 | 2/2007 | Minegishi et al. | |
| 7,208,092 B2 | 4/2007 | Micheli | |
| 7,241,272 B2 | 7/2007 | Karoor et al. | |
| 7,326,750 B1 | 2/2008 | Isik | |
| 2002/0123715 A1* | 9/2002 | Sorenson | A61M 1/1696 604/29 |
| 2003/0113931 A1* | 6/2003 | Pan | G01N 21/85 436/113 |
| 2003/0113932 A1 | 6/2003 | Sternberg et al. | |
| 2003/0114787 A1 | 6/2003 | Gura | |
| 2004/0260085 A1 | 12/2004 | Kriesel et al. | |
| 2005/0004539 A1 | 1/2005 | Brown et al. | |
| 2005/0015046 A1 | 1/2005 | Weber et al. | |
| 2005/0115462 A1 | 6/2005 | Disalvo et al. | |
| 2005/0175649 A1 | 8/2005 | Disalvo et al. | |
| 2006/0122560 A1 | 6/2006 | Burgmeier et al. | |
| 2006/0169635 A1 | 8/2006 | Zambianchi et al. | |
| 2006/0184112 A1 | 8/2006 | Horn et al. | |
| 2007/0079748 A1 | 4/2007 | Ahmed et al. | |
| 2007/0161113 A1 | 7/2007 | Ash | |
| 2007/0179461 A1 | 8/2007 | Sambasivam et al. | |
| 2007/0213665 A1 | 9/2007 | Curtin | |
| 2007/0264897 A1 | 11/2007 | Collias et al. | |
| 2008/0051696 A1 | 2/2008 | Curtin et al. | |
| 2008/0095822 A1 | 4/2008 | Maquet et al. | |
| 2008/0103444 A1 | 5/2008 | Jimenez | |
| 2008/0119805 A1 | 5/2008 | Brown et al. | |
| 2010/0100027 A1* | 4/2010 | Schilthuizen | A61M 1/3486 604/6.09 |

FOREIGN PATENT DOCUMENTS

| | | |
|---|---|---|
| EP | 2310068 B1 | 3/2012 |
| JP | 2005-533573 | 11/2005 |
| WO | 02/43859 A2 | 6/2002 |
| WO | 2006/061862 | 6/2006 |
| WO | 2007/103411 | 9/2007 |
| WO | 2008/024434 | 2/2008 |
| WO | 2008/075951 | 6/2008 |

OTHER PUBLICATIONS

Japanese Office Action for Japanese Application No. 2011-516792, dated Aug. 15, 2013.
Mexican Office Action dated Apr. 30, 2013 for related Mexican Appln. No. Mx/a/2010/014099.
Communication with Search Report for European Patent Application No. 12151971.4 dated May 16, 2012.
International Search Report and Written Opinion for International Application No. PCT/US2009/049152 dated Mar. 3, 2010.
C. Ronco, et al., "The Vicenza Wearable Artificial Kidney for Peritoneal Dialysis (ViWak PD)," Blood Purif. 2007; 25-383-388; DOI: 10.1159/000107775.
C. Ronco et al., "Does Nanotechnology Apply to Dialysis?," Blood Purif., 2001; 19:347-352.
N. Hoench, et al., "Haemodialysis Fluid: Composition and Clinical Importance," Blood Purif., 2007; 25:62-68; DOI: 10.1159;000096400.
A. Niessenson et al., "Continuously functioning artificial nephron system: The promise of nanotechnology," Hemodialysis International, 2005; 9:210-217.
A. Niessenson et al., "The Human Nephron Filter: Toward a Continuously Functioning, Implantable Artificial Nephron System," Blood Purif., 2005; 23:269-274; DOI: 10.1159/000085882.
M. Roberts, et al., "Innovative Peritoneal Dialysis: Flow-Thru and Dialysate Regeneration," Scholarly Review; ASAIO Journal, 1999 pp: 372-378.

\* cited by examiner

NANOCLAY SORBENT METHODS FOR USE WITH DIALYSIS

PRIORITY CLAIM

This application is a divisional application of U.S. patent application Ser. No. 15/816,550, filed Nov. 17, 2017, which is a continuation application of U.S. patent application Ser. No. 12/166,063, filed on Jul. 1, 2008, now U.S. Pat. No. 9,821,105, the entire contents of each of which are being incorporated herein by reference.

BACKGROUND

This patent relates generally to medical fluid delivery systems and methods. More particularly, this patent discloses systems, methods and apparatuses for portable, wearable systems with disposable cartridges that renew or refresh the dialysis fluid used for peritoneal dialysis or hemodialysis.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to control ultrafiltration, which is the process by which water (with electrolytes) moves across a membrane, such as a dialyzer or peritoneal membrane. For example, ultrafiltration in HD is a result of transmembrane and osmotic pressure differences between blood and dialysate across a dialyzer membrane. For a given osmotic pressure, the greater the transmembrane pressure the more rapid the ultrafiltration.

Problems exist with prior continuous flow systems, whether dealing with peritoneal dialysis or hemodialysis. One obvious problem is the quantity of fluid, often 120 liters or more, using during a hemodialysis treatment. The vast majority of the fluid is simply water, but the osmotic differential ingredients and the electrolytes are important for the dialysis process and the well-being of the patient. The same holds true for peritoneal dialysis, often conducted at home, where patients manage similarly large quantities of dialysis liquids which must be transported, stored, and then disposed of.

What is needed is a better way to conduct dialysis without the expense and inconvenience of large quantities of liquid dialysis fluids.

SUMMARY

One embodiment a wearable system for removing body wastes from a fluid. The wearable system includes a closed fluid loop for circulating peritoneal dialysis fluid to and from a peritoneum of a patient, at least one pump attached to the loop for circulating the peritoneal dialysis fluid into and out of the peritoneal cavity and through the fluid loop, a replaceable cartridge housing having an inlet and an outlet, and at least one nanoclay within the housing for removing at least one body waste from the peritoneal dialysis fluid, wherein the nanoclay includes a processed clay having at least one dimension from about 1 nm to about 200 nm, and a drain container connected to the closed fluid system loop for removing excess fluid.

Another embodiment is a wearable system for removing body wastes from a fluid. The wearable system includes a catheter having an inflow lumen and an outflow lumen in communication with a peritoneal cavity of the patient, a fluid circuit for circulating peritoneal dialysis fluid to and from the peritoneal cavity, a quantity of dialysate within the fluid circuit, at least one pump attached to the fluid circuit for circulating the peritoneal dialysis fluid into and out of the peritoneal cavity and through the fluid circuit, a replaceable cartridge housing having an inlet and an outlet, and at least one processed nanoclay within the housing for removing at least one body waste from the peritoneal dialysis fluid, wherein the nanoclay includes a processed clay having at least one dimension from about 1 nm to about 200 nm, a filter coupled to the fluid circuit for removing particulates and debris from the peritoneal dialysis fluid, and a discharge path coupled to the fluid circuit allowing the peritoneal dialysis fluid to be drained after a treatment period.

Another embodiment is a method for removing body wastes from a fluid. The method includes steps of circulating peritoneal dialysis fluid in a fluid circuit that includes a peritoneal cavity of a patient and a wearable dialysis system, absorbing wastes from the peritoneum during a dwell time within the peritoneum, pumping dialysis fluid from the peritoneum with a wearable pump forming part of the wearable dialysis system, removing wastes from the peritoneal dialysis fluid with a sorbent cartridge that includes at least one processed nanoclay having at least one dimension from about 1 nm to about 200 nm, and recirculating the peritoneal dialysis to the peritoneal cavity of the patient after the step of removing.

Another embodiment is a method for removing body waste of a patient. The method includes steps of providing a volume of peritoneal dialysis solution, pumping the peritoneal dialysis solution into a peritoneal cavity of the patient, pumping the peritoneal dialysis fluid from the peritoneal cavity using a wearable pump of a wearable peritoneal dialysis system to a wearable cartridge, removing wastes from the peritoneal dialysis fluid with the wearable cartridge using at least one processed nanoclay having at least one dimension from about 1 nm to about 200 nm, exchanging at least one of ammonium ions and phosphate ions of the peritoneal dialysis fluid for ions of the processed nanoclay, recirculating the peritoneal dialysis to the peritoneal cavity of the patient after the step of removing, filtering particulates and debris from the peritoneal dialysis fluid with a wearable filter during one of the steps of pumping or recirculating.

Another embodiment is a wearable replaceable cartridge. The wearable replacement cartridge includes a housing having an inlet and an outlet, the housing suitable for wearing by person, and at least one processed nanoclay within the housing for removing at least one body waste from a fluid, wherein the nanoclay includes a processed clay having at least one dimension from about 1 nm to about 200 nm.

Another embodiment is a method of making hollow fibers. The method includes steps of preparing a spinning solution of a polymer for a hollow fiber, preparing an infusing slurry of nanoparticles, a solvent used in the spinning solution and water, extruding the spinning solution through nozzles of a spinneret to form a hollow fiber, extruding the infusing slurry through a center of the spinneret into a lumen of the hollow fiber, sending the hollow fiber into a coagulation bath, gathering the hollow fiber, wherein the nanoparticles are within the lumen of the hollow fiber, and partially drying said hollow fiber.

Another embodiment is a method for refreshing and renewing dialysis fluid. The method includes providing a filter with processed nanoclay particles having at least one dimension from about 1 nm to about 200 nm, flowing a used dialysis fluid through the filter, absorbing waste product ions from the dialysis fluid by the processed nanoclay, and replacing the waste product ions with ions from the processed nanoclay particles to refresh and renew the dialysis fluid, wherein the refreshed and renewed dialysis fluid is capable of reuse as a dialysis fluid.

Additional features and advantages are described herein, and will be apparent from the following Detailed Description and the figures.

DETAILED DESCRIPTION

Figure 1:
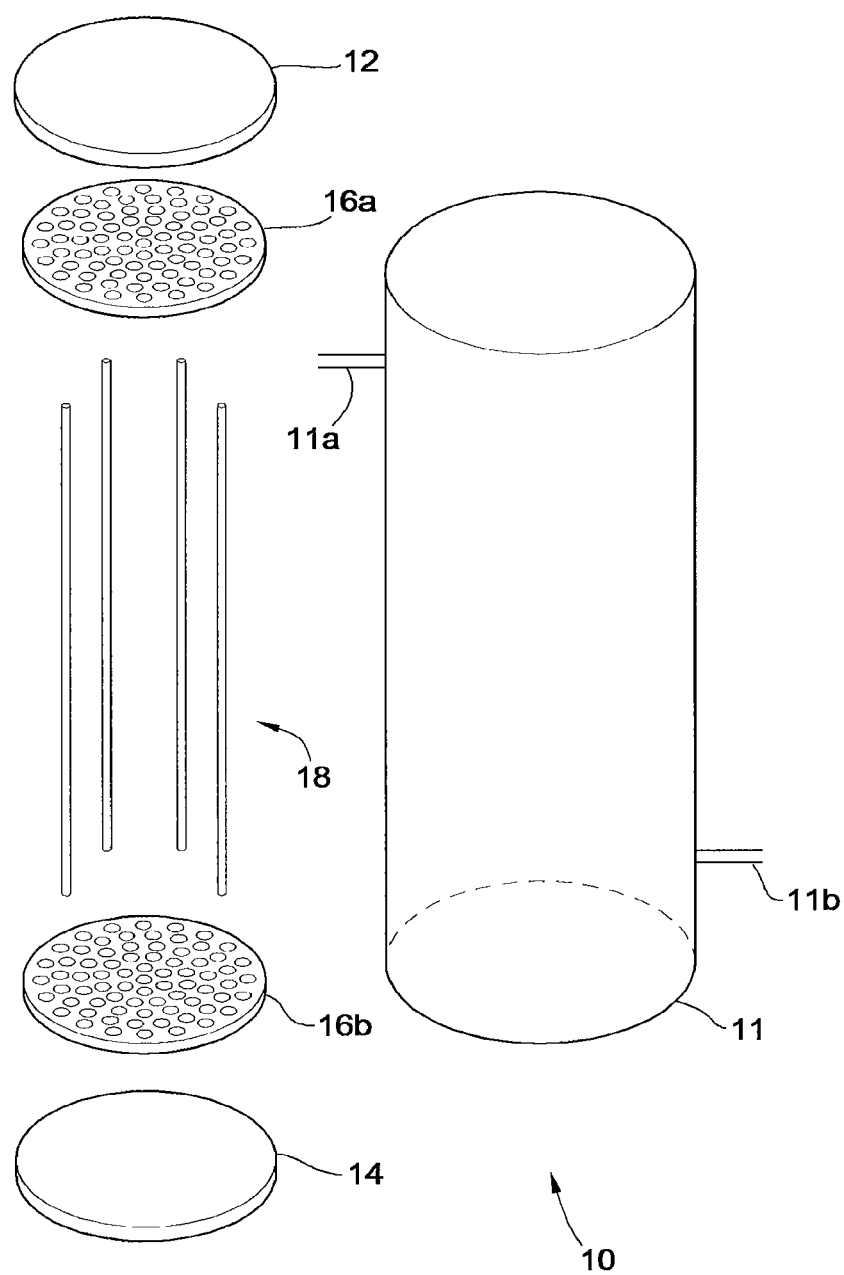
FIG. 1 depicts a sorption filter/ion exchange device.

Dialysis fluid may be cleansed and renewed by filtering body wastes from the fluid and adding the needed electrolytes and osmotic ingredients. See, e.g., U.S. Pat. No. 5,944,684, entitled, "Wearable Peritoneum-Based System for Continuous Renal Function Replacement and Other Biomedical Applications," to Martin Roberts et al., and an article in ASAIO Journal, entitled, "Innovative Peritoneal Dialysis: Flow-Thru and Dialysate Regeneration," by Martin Roberts et al. See also U.S. Pat. No. 7,208,092, entitled, "Systems and Methods for Peritoneal Dialysis," assigned to the assignee of the present patent. These three patents and articles describe the use of disposable cartridges to remove body wastes, such as urea, uric acid, creatinine, and $\beta_2$-microglobulin, among other wastes, from dialysis fluids. These systems typically use carbon or charcoal to remove impurities, urease to react urea into ammonia and ammonium ions, and zirconium oxide or zirconium phosphate to remove ammonium and phosphate ions.

Nanoclays Useful in Dialysis

In addition to using sorbents such as zirconium oxide, zirconium phosphate, and zirconium phosphate, it is possible to use such compounds or resins to exchange ions with the dialysis fluid. That is, by passing the dialysis fluid through a bed of one or more resins such as these, one can absorb undesirable ions, such as ammonium ($NH_4^+$) and phosphate ($PO_4^{-3}$) for more desirable ions, such as $K^+$, $Ca^{+2}$, $Mg^{+2}$, hydrogen ($H^+$), hydronium ($H_3O^+$), $Na^+$, bicarbonate $HCO_3^-$, hydroxide ($OH^-$), lactate ($CH_3CH(OH)COO^-$), acetate ($CH_3COO^-$) and chloride ($Cl^-$). Cation exchange resins are used for the positive ions, with anion exchange resins used for the negative ions. While not ionic, other species such as glucose may be added to the nanoclay or to the filter and absorbed by the dialysis fluid as it passes through the purification system.

Though commercial ion exchange resins may be used, the present disclosure reports on new ion exchange resins made from processed nanoclays. The starting materials for these nanoclays are typically layered clay minerals. The processed nanoclays, in general, have higher exchange capacities and thus can absorb more impurities, such as ammonium and phosphate, and impart higher quantities of beneficial species mentioned above. The ion exchange resins may be kept in separate beds or layers or may be intermixed. In the preparation of the ion exchange resins using nanoclays, each particular lot or amount of nanoclay is prepared with a specific ion for exchange at one time. For example, a particular batch of a basic clay may be mixed with sodium chloride to prepare for exchange of chloride for an anion of body waste, and a different batch of an acidic clay is mixed with sodium chloride to prepare for exchange of sodium ion for a cation of body waste, such as an ammonium ion.

Layered clay minerals can be used as starting materials for the nanoclay ion exchange resins, as outlined in U.S. patent application Ser. No. 10/979,364, which is hereby incorporated by reference in its entirety and relied on. These materials are processed or exfoliated to form nanoparticles or layers of nanoparticles. The layered clay minerals suitable for use in the present invention include those in the geological classes of the smectites, the kaolins, the illites, the chlorites, the attapulgites and the mixed layer clays. Typical examples of specific clays belonging to these classes are the smectites, kaolins, illites, chlorites, attapulgites and mixed layer clays. Smectites, for example, include montmorillonite, bentonite, pyrophyllite, hectorite, saponite, sauconite, nontronite, talc, beidellite, volchonskoite, stevensite, and vermiculite. Montmorillonite nanoclay is one good example. See U.S. Pat. No. 5,869,033, which is incorporated by reference herein. Other techniques include the intercalation techniques used in U.S. Pat. No. 7,326,750, which is hereby incorporated by reference.

Kaolins include kaolinite, dickite, nacrite, antigorite, anauxite, halloysite, indellite and chrysotile. Illites include bravaisite, muscovite, paragonite, phlogopite and biotite. Chlorites include corrensite, penninite, donbassite, sudoite, pennine and clinochlore. Attapulgites include sepiolite and polygorskyte. Mixed layer clays include allevardite and vermiculitebiotite. Variants and isomorphic substitutions of these layered clay minerals are also useful. Layered nanoclays may be either naturally occurring or synthetic. For example, natural or synthetic hectorites, montmorillonites, and bentonites may be used as the starting material for the particles of nanoclays.

Synthetic nanoclays may also be used in embodiments. With appropriate process control, the processes for the production of synthetic nanoclays does indeed yield primary particles that are nanoscale-sized. However, the particles are not usually present in the form of discrete particles, but instead predominantly assume the form of agglomerates due to consolidation of the primary particles. Such agglomerates may reach diameters of several thousand nanometers, such that the desired characteristics associated with the nanoscale nature of the particles cannot be achieved. The particles may be deagglomerated, for example, by grinding as described in EP-A 637616 or by dispersion in a suitable carrier medium, such as water or water/alcohol and mixtures thereof. All these and many other processes are included in the meaning of the term processed.

Synthetic materials for making suitable processed nanoclays include layered hydrous silicate, layered hydrous aluminum silicate, fluorosilicate, mica-montmorillonite, hydrotalcite, lithium magnesium silicate and lithium magnesium fluorosilicate. An example of a substituted variant of lithium magnesium silicate is one wherein the hydroxyl group is partially substituted with chloride. Lithium and magnesium may also be partially substituted by aluminum. Lithium magnesium silicate may be isomorphically substituted by any member selected from the group consisting of magnesium, aluminum, lithium, iron, chromium, zinc and mixtures thereof. Synthetic hectorite, for example, is commercially marketed under the trade name Laponite® by Southern Clay Products, Inc., Gonzalez, Tex., U.S.A., and may be used as a starting material for the nanoparticles. There are many grades or variants and isomorphous substitutions of the Laponite products, which include water-based rheological additives to aid in their dispersion and utility.

Other examples of synthetic materials available from Southern Clay Products, Inc., include bentonite clays which have been processed by one of the above means, and to which water-based rheological additives for improved dispersion have been added, such as the Gelwhite®, Mineral Colloid®, and Bentolite® and Permont® products. Still other products include modified processed bentonite clays which include a solvent-based rheological additive, such as the Claytone®, Garamite®, and Perchem® products. As one example, ethylene vinyl alcohol (EVA) may be used to help exfoliate the natural clay product.

Still other processed nanoclays are useful in embodiments of the present disclosure. Exemplary nanoclay materials include montmorillonite nanoclay materials and organically-treated montmorillonite nanoclay materials (i.e., montmorillonite nanoclay materials that have been treated with a cationic material that imparts hydrophobicity and causes intercalation), and equivalent nanoclays as are known in the art. Such materials are available from Southern Clay Products, Inc. of Gonzales, Tex. (e.g., Cloisite® series of nanoclays); Elementis Specialties, Inc. of Hightstown, N.J. (e.g., Bentone® series of nanoclays); Nancor, Inc. of Arlington Heights, Ill. (e.g., Nanomer® series of nanoclays); and Sud-Chemie, Inc. of Louisville, Ky. (e.g., Nanofil® series of nanoclays). A number of such materials are described in U.S. patent application Ser. No. 11/434,371, which is hereby incorporated by reference in its entirety and relied upon.

Yet other particular processed nanoclays are useful in embodiments. For example, Gelwhite® L, a hydrated aluminum silicate, has been useful, as has been Tixogel® VP-V, a quaternary ammonium bentonite, also available from Rockwood Additives, Princeton, N.J., USA. The quaternary ammonium bentonite is available as paste (about 1.8 g/cc) with a maximum 3% moisture content. Fulacolor® XW, also a commercial product from Rockwood Additives, has been useful. It is available as a dispersion with about 7% free moisture. Laponite® XLG, from Rockwood Additives, is a synthetic layered silicate that is available as a free-flowing powder. Another desirable processed nanoclay used for testing purposes is processed kaolinite, especially that available from Micromeritics Inc., Norcross, Ga., USA, P/N 004/16819/00, with a BET surface area of about 16 $m^2/g$.

Nanoclays and Treatment of Nanoclays

The urine from chronic kidney disease patients typically has a basic pH. For these patients, it has been found that acidic nanoclays are particularly useful for the absorption of urea from dialysis fluid. For example, Fulacolor® XW is considered an acidic nanoclay because a 2% suspension in water has a pH of about 3.5. Other acidic nanoclays include, but are not limited to, Fulacolor SR (also a pH of 3.5 for a 2% suspension in water), Fulcat 220 (pH 2.9), Fulcat 240, 400 and 435 (pH 3.0), and Fulcat 240 (pH 3.5). In addition, a variety of clays may be treated with acids, such as the Lewis acid $AlCl_3$, to reduce pH and render them better able to absorb ammonia or ammonium, by-products of urea from used dialysis fluid that is treated with urease. Lewis acids are generally defined as electron-pair acceptors, including acceptors such as $AlCl_3$ and $BF_3$, and mineral acids, such as HCl, $HNO_3$, sulfuric acid, and the like.

Examples of treatable clays include at least Gelwhite L and Laponite XLG. Both of these clays had alkaline pH values, from about 8.5 to about 9.8, a 2% suspension in water. They were treated by mixing the clay particles in a solution or suspension in deionized water, and then rinsed to insure there was no residual $Cl^-$. It should be noted that some compositions of clays are unstable when treated; the clays that are responsive to increase absorption without layer collapse should be used.

In one example, anhydrous 99% pure granular $AlCl_3$ was mixed with deionized water to form a 0.2 M solution. 25 g of Gelwhite L or 25 g. Laponite XLG was then added to about 250 ml 0.2 M $AlCl_3$ solution to achieve a ratio of about 2 mM (Al III) per gram of clay. The resulting slurries were stirred moderately for 24 hours. The clay samples were then washed with pure water and sampled. Washing was stopped when no $Cl^-$ was observed visually upon the addition of $AgNO_3$. The $Al^{+3}$ fortified clay samples were vacuum dried at 60° C. for 24 hours and were then used in urea-uptake experiments.

Subsequent experiments were conducted with about 1 g of nanoclay sample in 10 ml of Baxter Dianeal® PD-4 dialysis fluid with 60 mg/dl urea. The samples were kept at body temperature and depletion of urea from the solution, uptake by the nanoclay, were observed. In this treatment, the naturally acidic nanoclays were best, followed by the treated nanoclays, which showed about a 30 percent increase in uptake following treatment. It is not necessary to confine the acidification to strictly Lewis acids only, such as aluminum chloride, aluminum nitrate, aluminum sulfate, and stannic chloride. Mineral acids, such as hydrochloric acid, sulfuric acid, nitric acid, and so forth, generally electron-pair acceptors, may also be used, without the possibility of releasing additional aluminum.

In addition, sorbents, such as nanoclays, may be treated with other substances, such as an enhancing agent, that are known to enhance the uptake of molecules with an amine functional group, such as ammonia or ammonium. For example, clays or standard polystyrene beads may be treated with compounds including glyoxal or a glyoxal group to enhance their ability to absorb urea or ammonium. These include phenylglyoxal, 4'-(trifluoromethyl)phenylglyoxal, 2'-chlorophenylglyoxal, 2'-4'-dimethlylphenylglyoxal and 2'-fluorophenylglyoxal. Styrene ion exchange resins treated with any of these had excellent urea uptake measurements, from about 20 mg urea/g glyoxal to about 100 mg urea uptake/g glyoxal.

Nanoclays as used herein means clays made from particles (including but not limited to rod-shaped particles, disc-shaped particles, platelet-shaped particles and tetrahedral-shaped particles), fibers, nanotubes, or any other materials having dimensions or spacings between layers on the nano scale. The spacing between layers may occur as a result of exfoliation, intercalation, expansion, or other treatment of the clay or mineral in question. In one embodiment, the nanoclays have an average particle size of about 1 to about 1000 nanometers, preferably 2 to about 750 nanometers. That is, the nanoclays have a largest dimension (e.g., a diameter or length) of about 1 to 1000 nm. Nanotube-shaped nanoclays can include structures up to 1 centimeter long, alternatively with a particle size from about 2 to about 50 nanometers. Nanoclay particles have very high surface-to-volume ratios. The nanoparticles may be crystalline or amorphous. A single type of nanoclay may be used, or mixtures of different types of nanoclays may be used. If a mixture of nanoclays is used, the clays may be homogeneously or non-homogeneously distributed in a composite material or a system or composition containing the composite material. Other natural materials, or enhanced materials, such as zeolites or natrolite, a particular hydrated sodium silicate zeolite, may also be used.

Non-limiting examples of suitable particle size distributions of nanoclays are those within the range of about 2 nm to less than about 750 nm, alternatively from about 2 nm to less than about 200 nm, and alternatively from about 2 nm to less than about 150 nm. It should also be understood that certain particle size distributions may be useful to provide certain benefits, and other ranges of particle size distributions may be useful to provide other benefits. For instance, color enhancement requires a different particle size range from that for other properties. The average particle size of a batch of nanoclays may differ from the particle size distribution of those nanoclays. For example, a layered synthetic silicate can have an average particle size of about 25 nanometers while its particle size distribution can generally vary between about 10 nm to about 40 nm. It should be understood that the particle size distributions described herein are for nanoclays when they are dispersed in an aqueous medium. The average particle size is based on the mean of the particle size distribution.

The nanoclays are more useful when they have been processed, deagglomerated, expanded, or exfoliated to a form that allows the dialysis fluid to percolate through the nanoclay particles. In this manner, the particles can absorb impurities or can release a desirable anion or cation into the dialysis fluid in exchange for an undesirable anion or cation. It is important that the nanoclay or ion exchange resin have a small particle size, as noted, so that it can intimately contact the dialysis fluid and have the opportunity for adsorption, absorption, or exchange with the fluid.

Sorption and Exchange Devices

The nanoclays described above may be incorporated in a variety of devices used to sorb waste products from dialysis fluid of patients with kidney disease. The devices may take on many forms, including a flat or cylindrical filter-shaped object, e.g., a flat filter with tiny nanoclay particles encapsulated between permeable membrane end-caps.

Alternatively, the sorption and exchange devices may be in a shape consistent with shell and tube heat exchangers, i.e., a plurality of fibers that encapsulate or include nanoclay particles, the plurality arranged in a linear bundle of fibers in a cylindrical housing, the fibers capped on both ends or near both ends. The fibers may be typical dialysis fibers, such as those used in hemodialysis, that is, fibers made from polyethersulfone (PES) and having an outer diameter of 1.5 micrometers, an inner diameter of about 1.1 micrometers, and a wall thickness of about 0.20 micrometers. Such fibers typically have a molecular weight cut off (MWCO) of about 50K Daltons, that is, they are permeable to molecules having a molecular weight of up to that size, but not more. In one embodiment, the dialysis liquid which is being filtered or purified flows into a side of the housing near one end, flows around the fibers, and then exits at 180° on the side near opposite end of the housing.

In testing and experiments, other fibers were also used. For example, experimental fibers several orders of magnitude larger were prepared, having an outer diameter of 1.5 millimeters, an inner diameter of about 1.1 millimeters, and a wall thickness of about 0.20 millimeters, and having a pore size of about 0.4 micrometers, with a MWCO from about 50K Daltons to about 120K Daltons. With these fibers, it is possible to use a needle, such as a 19 gauge needle, to inject a nanoparticle slurry or paste into each fiber. The nanoparticles remain after the fibers are dried and the water or other solvent driven off.

A first embodiment of a sorption device or ion exchange device is depicted in FIG. 1. The device 10 includes a housing 11 with an inlet connection 11a and an outlet connection 11b. The housing has the general shape of a right cylinder and the connection are on opposite sides, about 180°, and are near the ends of the housing 11. The device includes a plurality of hollow fibers 18, the hollow fibers potted into end sheets 16a, 16b on opposite ends of the fibers. In this embodiment, the flow of dialysis liquid does not penetrate through the end sheets, but halts at the end sheets. The housing includes top and bottom caps 12, 14, for sealing the housing 11 after assembly.

Figure 2:
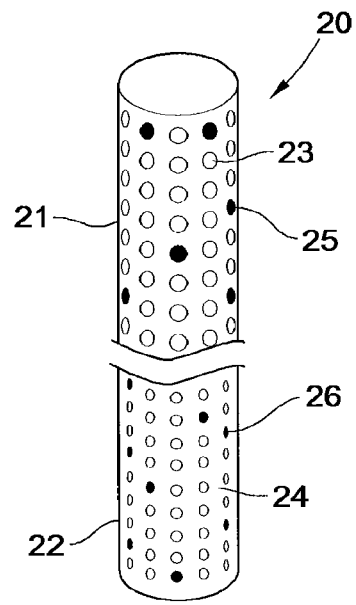
FIG. 2 depicts a hollow fiber suitable for use in a sorption filter/ion exchange device.

The fibers 18 may be as depicted in FIG. 1, or may instead be as shown in FIG. 2. A fiber 20 in FIG. 2 includes an upper portion 21 with a plurality of pores 23 and a second plurality of nanoclay particles 25 which were formed in the pores of the fiber. As is well known to those with skill in dialysis arts, the fiber may not be entirely uniform. Thus, a bottom portion 22 of the same fiber may have pores 24 that are smaller in size, and the pores 24 in this embodiment have captured or formed around additional nanoclay particles 26, these particles smaller than particles 25 in the upper portion 21. The nanoclay particles may be considered as plugging the pores of the fiber, while in reality the fiber has actually been formed around the particles.

In other embodiments, the same or similar fibers are used, but are not capped on their ends, and the housing does not have side ports for inlet and outlet of dialysis liquid. In these embodiments, the fibers themselves may be packed with tiny nanoparticles that sorb waste products or exchange ions with the dialysis fluid. For example, it is possible to inject a liquid or paste slurry with nanoparticles into the fibers.

Figure 3:
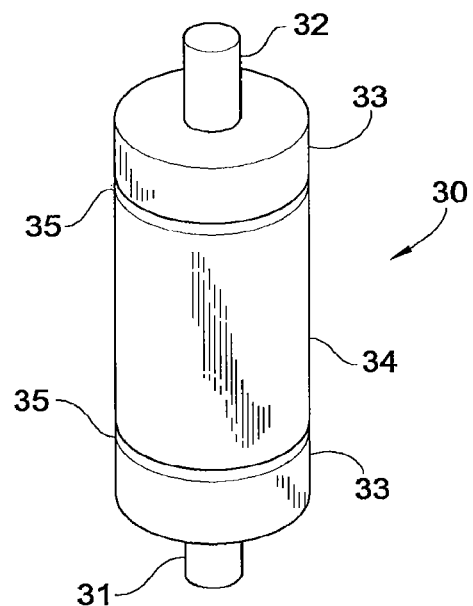
FIG. 3 depicts an alternate embodiment of a sorption filter/ion exchange device.

A third embodiment of a sorption filter is depicted in FIG. 3. Sorption filter 30 includes inlet and outlet ports 31, 32, end portions 33 and a central portion or housing 34. The end portions 33 are separated from the central portion by permeable membranes or seals 35. This embodiment functions by having at least two different purifying functions. At least one end 33, such as the end portion near inlet port 31, includes filtering activated carbon or charcoal. Activated carbon or charcoal is known to remove heavy metals, oxidants, and waste products. The next portion, the central portion 34, includes the hollow fibers with nanoclay discussed above. This portion, which may also include urease, is used to convert urea into ammonium ions, which is easily absorbed by a strong acid ion exchange resin, such as an acidic nanoclay. This portion also absorbs phosphate, creatinine, and other waste products. The opposite end portion 33, near the outlet 32, may include additional activated carbon, or may include another known ion exchange/sorption resin, such as zirconium oxide, to better remove a different waste, such as sulfate and phosphate from the dialysis fluid.

Formation of Hollow Fibers

The fibers may instead be made from a standard phase inversion process, the phase including particles of nanoclays as part of the phases. Phase inversion processes are described in details in several issued U.S. patents, including the following, each of which is hereby incorporated by reference in its entirety: U.S. Pat. Nos. 4,035,459; 4,219,517; 5,403,485; 5,656,372; 5,833,896; and 5,859,175. A typical phase inversion process includes a polymer, a solvent, and a non-solvent or pore-former. The solution as described is mixed, and a quantity of nanoclay is added as a part of the pore-former. The solution and particles and pumped through a spinneret and hollow fibers are formed, with pores formed by the non-solvent and nanoclay particles. During phase separation, gelation and polymerization takes place, and the nanoclay particles form part of many of the pores, i.e., they are attached as particles in the pores of the fibers. As one example, polyethersulfone (PES) fibers are formed using a PES polymer as a hydrophobic resin and polyvinylpyrrolidone (PVP) as a hydrophilic resin, and N-methyl-pyrrolidone (NMP) as a solvent, with water as the non-solvent. A small quantity of nanoclay particles are stirred into the mixture, which is then cast into a thin film or extruded through the nozzle of a spinneret and coagulated in a water bath to form a hollow fiber. Nanoclay particles are used in the spinning solution at about 0.1% to about 3% by weight.

Formation of Hollow Fibers with Embedded Nanoparticles

It is also possible to prepare fibers with nanoparticles embedded within. For example, in the preparation of PES dialysis fibers, a spinneret is used to extrude a fiber-forming polymer solution, typically a polymer and a solvent, around a central core solution which is mostly water or other solvent, and is used to control the size or inner diameter of the fibers. In most situations, the central core or infusing solution is simply water or other solvent which evaporates or is otherwise disposed of. The fiber-forming solution extruded around the core polymerizes and becomes the hollow fiber, as described in U.S. Pat. Nos. 5,938,929, 6,103,117, and 7,182,870, which are hereby incorporated by reference in their entirety. The core liquid is a thin slurry of nanoparticles in a liquid, with the liquid providing a wetting agent for wetting the inside of the formed fiber. The particles remain within the fiber lumen after the water or other solvent evaporates from the inside of the fibers so formed. Using this method avoids the time-consuming and laborious techniques otherwise required for insertion into the fibers.

In one embodiment, the polymer is a hydrophobic resin, such as a polysulfone, and a hydrophilic resin, such as polyvinylpyrrolidone (PVP), or a modified polyvinylpyrrolidone, such as a PVP-copolymer. The hydrophilic resin may also be polyethylene glycol or polyvinyl acetate. The spinning solution also includes a solvent that dissolves both the hydrophobic resin and the hydrophilic resin. Solvents useful for this purpose include demethylacetamide (DMAC), dimethylformamide (DMF), dimethylsulfoxide (DMSO), N-methyl-2-pyrrolidone (NMP), and dioxane. The spinning solution also includes an additive, normally a small amount of water or a lower alcohol, such as methanol, ethanol, isopropyl alcohol, hexanol, or 1,4-butanediol. The additive should be compatible with the solvent, and should be a good solvent for the hydrophilic polymer but not a good solvent for the hydrophobic polymer. The additive is used to help coagulate the hollow fiber, and in the case of polysulfone, may be present at about 1.0 to 1.7 percent of the spinning solution. For other polymers, other concentrations of additive, typically water, are used.

The infusing solution, or slurry, is typically made from the same solvent used for the spinning solution, with a higher quantity of water, e.g., 65 parts DMAC and 35 parts water is used with a small quantity, 0.1 to 5 percent, of clay nanoparticles. In some processes, a double spinneret is used. In these cases, the polymer solution is discharged from the outer tube of the spinneret, while the infusing slurry is extruded into the hollow section of the inner tube of the spinneret. The fiber leaves the spinneret and enters a high-humidity air "dry zone" before it is sent to a coagulation bath, where coagulation takes place and a hollow fiber membrane is formed. The coagulation bath is typically water with about 20% solvent, such as DMAC, at a temperature from about 40-50° C. After coagulation, the fiber is washed with water and then immersed into a wetting solution to prevent drying. An aqueous alcohol solution is useful as a wetting solution, with the useful alcohols including glycerine, ethylene glycol, polypropylene glycol and polyethylene glycol.

The fiber is then cut to proper lengths and a filter is formed by laying up a plurality of the cut lengths and potting the ends of the lengths. Epoxy or other medically-acceptable plastic material may be used. A fine screen may be used to help retain the nanoparticles within the hollow fibers. The filter or purifying device is then placed into a housing so that the proper plumbing connections may be made.

Other hollow fibers useful for dialysis generally or for refreshing dialysis solutions include cellulose acetate and polyvinylidenefluoride (PVDF) fibers. PVDF fiber construction is described in U.S. Pat. No. 7,182,870, which is hereby incorporated by reference in its entirety. The method generally follows that described above for PES fibers. A PVDF-polymer is dissolved in a "poor" solvent, such as cyclohexanone or γ-butylactone. An infusing solution is also used, such as a solution of the solvent and water, e.g., a solution of 60 to 100 percent solvent, with the remainder water, and with about 0.1% to about 5% nanoparticles. Other fibers may be formed from other polymers, with the nanoparticles embedded during manufacture.

Wearable, Portable Dialysis Systems

The fibers, filters, sorption devices, and ion exchange devices described above are used in a wearable, portable dialysis system. These devices are particularly applicable to peritoneal dialysis, as shown below in FIGS. 4-5. However, these same techniques are applicable to hemodialysis. Hemodialysis is known to require huge amounts of dialysis fluid, up to 120 liters per treatment. Any technique that would allow refreshment and reuse of the dialysis fluid for hemodialysis treatment would be a great advantage for patients and caregivers alike.

Figure 4:
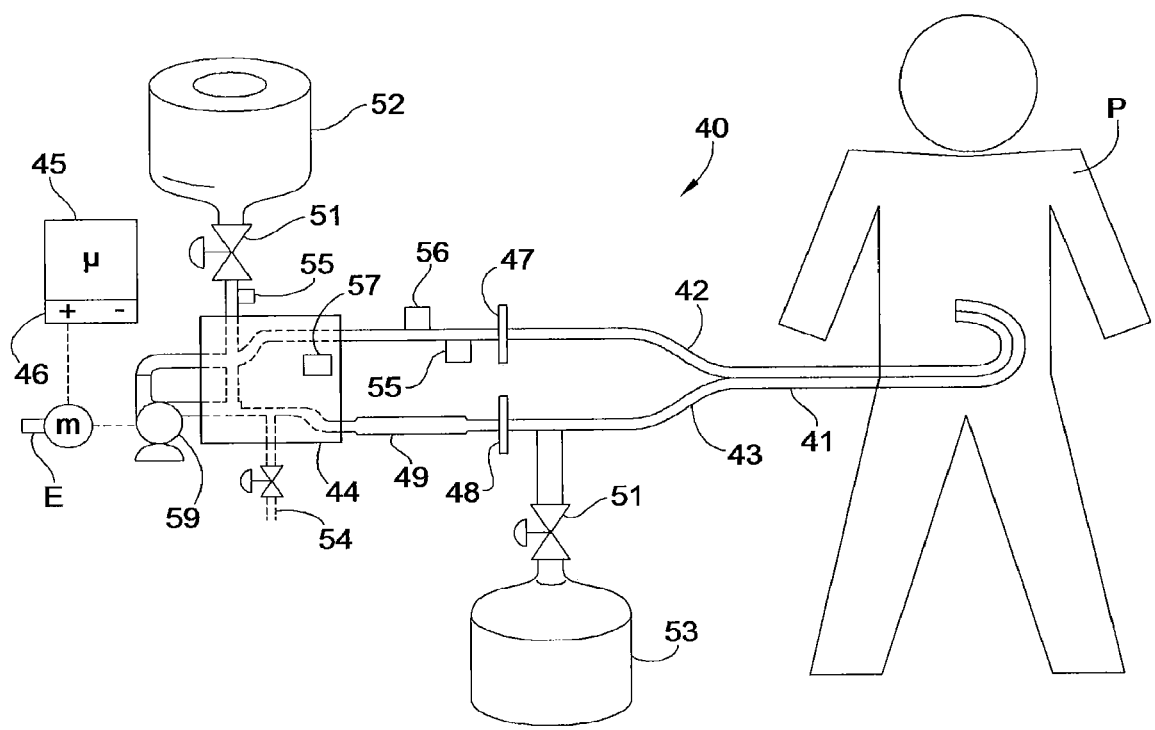
FIG. 4 depicts a first embodiment of a wearable portable kidney using a sorption filter/ion exchange device

FIG. 4 depicts a first embodiment or system 40, in which there is a single pump 59. The pump 59 may be connected to the desired inputs and outputs via connector block 44, using internal valves and connectors. The connector block in this sensor functions in a manner similar to that of a dialysis cassette, but the connector block needed for this system is much simpler. System 40 includes a patient access device 41, such as a double-lumen catheter suitable for infusing and withdrawing dialysis fluid to and from a patient P. Access device 41 has an input lumen 42 and an output lumen 43. The tubing connecting the output lumen 43 to the other components has a valve 51, as shown, for connecting to a drain 53, for draining via gravity flow upstream of the connector block. With the proper valves open and others closed within connector block 44, the pump will suction spent dialysate from the patient through a particulate filter 48 and then through the sorption device/ion exchange device 49.

The connector block is a plastic, disposable cassette that allows connection of inlet and outlet tubing. The connector block also includes a plurality of simple valves that allow a user to route the flow of dialysis fluid from a desired input to a desired output destination. The valves may be simple, two-way, on-off valves or may be slightly more complicated three-way valves. For example, a first three-way valve may be used to route input used dialysis fluid to sample port 54 or to pump 59, and a second three way valve may be used to connect a source 52 of fresh dialysis fluid to the pump output. It will be understood that several two-way valves may be used instead.

The refreshed dialysate is then connected via tubing to the patient input lumen 42 through an optional antimicrobial or antibacterial filter 47. If some or all of the spent dialysate is drained, fresh dialysis liquid from connectable container 52 may be routed through its valve 51 into the connector block 44, through the filter 47, and then to patient inlet lumen 42.

Sample port 54 allows a user to take a sample of the dialysis fluid after it has been routed through the sorption/ion exchange device 49. Then connector block may also have an ammonia sensor 57, connected so that it is in contact with dialysis fluid which has been purified or treated by device 49. The operation of the ammonia sensor is explained below. In addition, samples may be taken upstream of the device 49 from drain bag valve 51.

The pump 59 is powered by a power source 46, such as a battery. System controller 45 is also powered by power source 46 and may monitor a temperature sensor 55 for the fresh dialysis liquid inlet, or the inlet to the patient, and may also monitor a pressure sensor 56 for an outlet of pump 59. The pump may also have a pressure sensor on its inlet side. Pump 59 is any suitable pump, such as a peristaltic roller pump with a motor M. The flow of dialysis fluid may be monitored using an encoder E or other suitable sensor for the pump. Other pumps may be used. It will be understood that a battery is the most convenient power source for a wearable, portable system as described herein. The power source may also be equipped with the necessary power conversion circuitry to accept household or clinic electrical AC power and convert the AC power to a DC voltage more useful in a portable system. Thus, a person may wear and use these smaller and more convenient systems using a non-portable power source.

Figure 5:
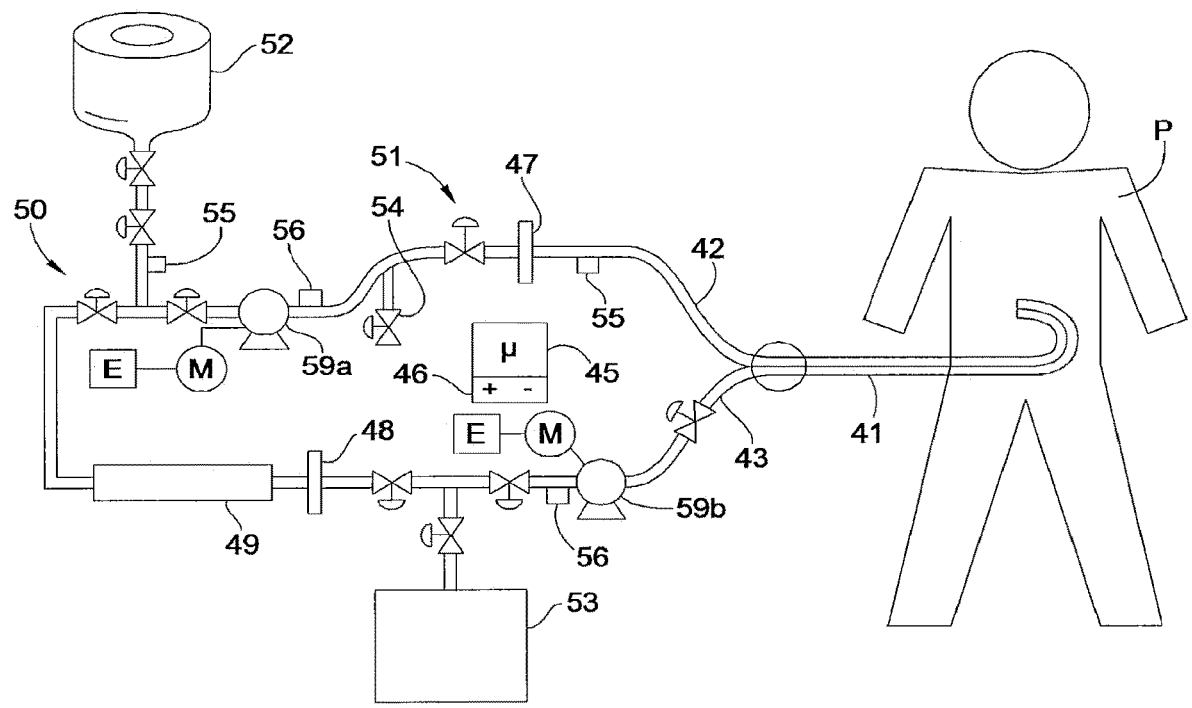
FIG. 5 depicts a second embodiment of a wearable portable kidney using a sorption filter/ion exchange device.

A second embodiment is depicted in FIG. 5. Wearable system 50 includes many of the same components shown in FIG. 4, but there is a second pump 59b in addition to first pump 59a, and the pumps are connected in a changeable but more definite manner. Inlet access device 41 includes an outlet lumen 43 connected via a valve to pump 59b, the pump powered by motor M. An encoder E on the motor keeps track of the pump armature position and thus can monitor dialysis liquid flow. The outlet of pump 59b may be routed to drain 53 or to the particulate filter 48 and sorption device/ion exchange device 49. Using the appropriate valves, the purified or refreshed dialysis liquid is then routed to second pump 59a, through filter 47, and to patient input lumen 42.

The spent dialysis fluid may instead be routed to drain 53, and substitute fresh dialysis fluid from container 52 infused into the patient. As before, system 50 is powered by battery 46 and controlled by microprocessor 45. Suitable temperature sensors 55 and pressure sensors 56 are used, in this instance also including a temperature sensor 55 to indicate the temperature of fresh dialysate from container 52, which should be warmed to body temperature, about 37° C., before infusion to the patient. This embodiment also has two sample ports for taking samples of the dialysis fluid. A sample may be taken just upstream via the valve near the drain bag 53. In addition, a sample port 54 near the patient inlet allows a user to test the fluid en route to the patient. The sample from sample port 54 may be useful for taking a sample to determine whether the fresh dialysis liquid is indeed fresh, or whether the spent dialysis fluid has been sufficiently refreshed or cleaned by device 49.

Ammonia Sensor or Urea Indicator

In one embodiment, the systems described above may be run virtually continuously, with a low flow of dialysis liquid continually being circulated through the sorption/ion exchange device 49. Waste products are thus continuously being adsorbed onto the device, while refreshed or renewed dialysis fluid is returned to the patient. It is useful to know whether the dialysis fluid is indeed being sufficiently cleansed, or cleansed at all by the sorption device. If the cleansed fluid has a high concentration of urea or its by-product ammonia, on the order of 20 to 50 ppm, it may be time to drain the spent dialysis fluid and replace it with fresh. As the dialysis liquid contacts urease, the urea is changed to ammonia, i.e. ammonia or ammonium ion, depending on the pH of the dialysis liquid, which is then removed by the nanoclays. As the nanoclays reach their capacity, less ammonia or ammonium is absorbed and the concentration of ammonia or ammonium, or both, increases and is detected by the sensor.

Figure 6:
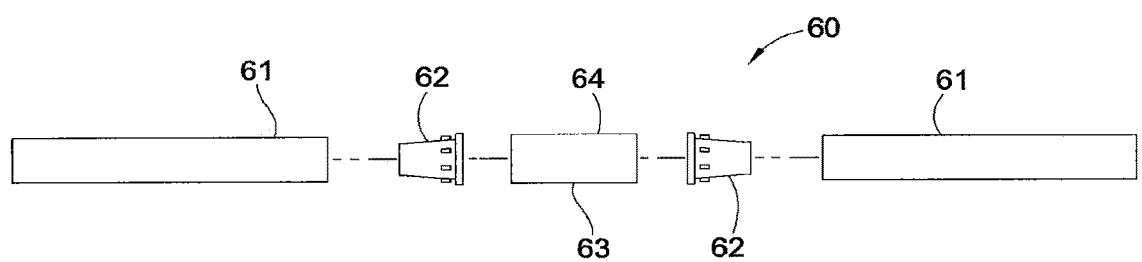
FIG. 6 depicts a sensor for detecting a condition of the dialysis fluid.

Ammonia sensors are disclosed in U.S. patent application Ser. No. 10/024,670, which is assigned to the assignee of the present disclosure. In addition, optical-type ammonia sensors are also disclosed in U.S. patent application Ser. No. 11/443,709. These sensors detect levels of ammonia based on the color changes. The detected level can be sent to a controller for a readout or indication of the level, which may be monitored continuously. Other methods to detect ammonia or urea in the dialysis fluid may also be used, such as a colorimetric method that takes advantage of the use of color change of a dye. The tubing used to connect the patient inlet or outlet to the system may include a color-changing sensor, as depicted in FIG. 6. Indicator 60 is connected to a dialysis purification system via tubing 61 and connectors, such as barbed connectors 62. The sensor includes a housing 63 with the color-changing substance 64 within the housing. The sensor allows passage of the dialysis liquid to and from the sensor and allows contact of the dialysis liquid with the color-changing substance.

The color-changing substance may be a dye. For example, a bromophenol blue dye will change from yellow to blue when the concentration of ammonium reaches 20 ppm. A similar color change is expected from bromothymol blue dye, and is also a yellow-to-blue change. At least these two dyes are especially useful because they are believed to respond to the concentration of ammonium, rather than simply a pH increase. Other suitable dyes may include bromocresol purple (yellow to blue), phenol red (red to yellow), methyl red (pink to yellow), morin hydrate (yellow to red), cresol red (red to purplish). These color changes may be used to indicate to an increased or increasing ammonia concentration. Other suitable dyes may also be used.

In addition, there are numerous other ways to test for ammonia, such as discrete ammonia sensor devices, or even test strips, such as those available from Hach Co. Loveland, Colo. 80539, USA. While not as convenient, other quantitative techniques may also be used, such as the Quanti-Chrom™ Urea Assay Kit available from BioAssay Systems, Hayward, Calif. 94545. The kit allows the quantitative determination of urea in biological samples and may also be used to test samples of water, such as dialysis fluid.

The ammonia sensor is desirably placed downstream of the sorbent column/ion exchange device, or if the sensing is done by manually taking samples, from a sample of dialysis fluid that has been treated. In this way, one can determine whether it is time to change or refill the disposable sorbent column/ion exchange device. Ammonia is convenient because it is a significant by-product of urea. Creatinine or other waste products may also be used, but they are typically not as convenient to detect as urea or ammonia. For example, creatinine may be continuously monitored by a spectrophotometer.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method for refreshing a used dialysis fluid, the method comprising:
   providing a filter with processed nanoclay particles having at least one dimension from 1 nm to 200 nm, the processed nanoclay particles chemically enhanced with an acid to increase urea uptake;
   flowing the used dialysis fluid through the filter so that the processed nanoclay particles absorb waste product ions from the used dialysis fluid; and
   replacing the waste product ions with ions from the processed nanoclay particles to refresh the used dialysis fluid, wherein the refreshed used dialysis fluid is capable of reuse as a dialysis fluid.

2. The method of claim 1, wherein the dialysis fluid is a hemodialysis fluid.

3. The method of claim 1, wherein the filter used for refreshing the used dialysis fluid comprises hollow fibers, and wherein the processed nanoclay particles are contained within a wall or a lumen of the hollow fibers.

4. The method of claim 1, wherein the ions from the processed nanoclay particles used for replacement are selected from the group consisting of: sodium, calcium, potassium, magnesium, chloride, acetate, bicarbonate and lactate.

5. The method of claim 1, comprising testing the used dialysis fluid for a concentration of one of the waste product ions.

6. The method of claim 1, wherein the processed nanoclay particles are selected from the group consisting of: expanded clays, exfoliated clays, intercalated clays, and substituted clays.

7. The method of claim 1, wherein the processed nanoclay particles include at least one of a smectite, a kaolin, an illite, a chlorite, an attapulgite, and a combination thereof.

8. The method of claim 1, wherein the processed nanoclay particles comprise swellable nanoclays selected from the group consisting of: smectite nanoclays, sepiolite nanoclays, zeolite nanoclays, palygorskite nanoclays, and mixtures thereof.

9. The method of claim 1, wherein the processed nanoclay particles are selected from the group consisting of: processed montmorillonite clay, processed bentonite clay, processed kaolin, processed talc, and processed vermiculite.

10. The method of claim 1, wherein the processed nanoclay particles include a cationic ion exchange compound.

11. A method for performing peritoneal dialysis comprising:
    pumping a peritoneal dialysis fluid into a peritoneal cavity of a patient;
    absorbing body wastes into the peritoneal dialysis fluid while inside the peritoneal cavity to form a used peritoneal dialysis fluid;
    pumping the used peritoneal dialysis fluid from the peritoneal cavity and into a cartridge;
    removing body wastes from the used peritoneal dialysis fluid via the cartridge to form a refreshed peritoneal dialysis fluid, wherein the cartridge includes at least one processed nanoclay having at least one dimension from 1 nm to 200 nm, and wherein the at least one processed nanoclay is chemically enhanced with an acid to increase urea uptake; and
    pumping the refreshed peritoneal dialysis fluid from the cartridge to the peritoneal cavity of the patient after the step of removing.

12. The method of claim 11, further comprising exchanging ammonium from the used peritoneal dialysis fluid while within the cartridge with at least one cation from the at least one processed nanoclay.

13. The method of claim 11, further comprising exchanging phosphate ions from the used peritoneal dialysis fluid while within the cartridge with at least one anion from the at least one processed nanoclay.

14. The method of claim 11, further comprising filtering particulates and debris from the used peritoneal dialysis fluid.

15. The method of claim 11, wherein the cartridge is a sorbent cartridge, and which includes further removing the body wastes using at least one of urease, zirconium oxide, zirconium phosphate, and zirconium carbonate provided by the sorbent cartridge.

16. The method of claim 11, wherein pumping the used peritoneal dialysis fluid is performed via a wearable device worn by the patient and providing the cartridge.

17. A method for performing peritoneal dialysis comprising:
    providing a volume of a peritoneal dialysis solution;
    pumping the peritoneal dialysis solution into a peritoneal cavity of a patient;
    pumping a used peritoneal dialysis fluid from the peritoneal cavity;
    filtering particulates and debris from the used peritoneal dialysis fluid using a filter;
    removing body wastes from the used peritoneal dialysis fluid while within a cartridge including at least one processed nanoclay having at least one dimension from 1 nm to 200 nm, the at least one processed nanoclay chemically enhanced with an acid to increase urea uptake;
    exchanging at least one of ammonium ions and phosphate ions from the used peritoneal dialysis fluid with ions from the at least one processed nanoclay; and
    pumping a refreshed peritoneal dialysis fluid from the cartridge to the peritoneal cavity of the patient.

18. The method of claim 17, wherein the step of exchanging comprises regeneration of the used peritoneal dialysis fluid by removing the ammonium ions and the phosphate ions and adding the ions of at least one of calcium, magnesium, chloride and lactate from the at least one processed nanoclay.

19. The method of claim 17, wherein the filter is a first filter and which further includes filtering bacteria and microorganisms from the used peritoneal dialysis fluid using a second, antimicrobial filter.

20. The method of claim 17, further comprising converting urea in the used peritoneal dialysis fluid to the ammonium ions using urease provided in the cartridge.

* * * * *